United States Patent [19]

Hampton et al.

[11] Patent Number: 4,940,062
[45] Date of Patent: Jul. 10, 1990

[54] GUIDING MEMBER WITH DEFLECTABLE TIP

[75] Inventors: Hilary J. Hampton, Santa Clara; John W. Gaiser, Mountain View; Charles S. Taylor, San Francisco; Timothy R. Machold, Moss Beach, all of Calif.

[73] Assignee: Advanced Cardiovascular Systems, Inc., Santa Clara, Calif.

[21] Appl. No.: 199,099

[22] Filed: May 26, 1988

[51] Int. Cl.⁵ .............................................. A61M 25/00
[52] U.S. Cl. .................................... 128/772; 128/657; 604/95
[58] Field of Search ................ 604/95; 128/4–6, 128/657, 772

[56] References Cited

U.S. PATENT DOCUMENTS

| | | |
|---|---|---|
| 3,452,742 | 7/1969 | Muller . |
| 3,521,620 | 7/1970 | Cook . |
| 3,528,406 | 9/1970 | Jeckel et al. . |
| 3,547,103 | 12/1970 | Cook . |
| 3,552,384 | 1/1971 | Pierie . |
| 3,749,086 | 7/1973 | Kline et al. . |
| 4,215,703 | 8/1980 | Willson . |
| 4,456,017 | 6/1984 | Miles . |
| 4,498,482 | 2/1985 | Williams . |
| 4,548,206 | 12/1985 | Osborne . |
| 4,676,249 | 6/1987 | Arenas et al. . |
| 4,719,924 | 1/1988 | Crittenden . |
| 4,732,163 | 3/1988 | Bonello et al. ........................ 604/95 |
| 4,748,986 | 6/1988 | Morrison et al. .................... 128/772 |
| 4,757,827 | 7/1988 | Buchbinder et al. ................ 128/657 |
| 4,787,399 | 11/1988 | Bonello et al. ...................... 128/657 |
| 4,798,598 | 1/1989 | Bonello et al. ...................... 128/772 |
| 4,799,496 | 1/1989 | Hargreaves ......................... 128/657 |
| 4,800,890 | 1/1989 | Cramer ................................ 128/657 |
| 4,813,434 | 3/1989 | Buchbinder et al. ................ 128/657 |
| 4,815,478 | 3/1989 | Buchbinder et al. ................ 128/657 |

*Primary Examiner*—Stephen C. Pellegrino
*Assistant Examiner*—Ralph Lewis
*Attorney, Agent, or Firm*—Fulwider, Patton, Lee & Utecht

[57] ABSTRACT

The invention is directed to a guiding member for vascular catheters, particularly dilatation catheters for angioplasty procedures having a deflectable tip. The guiding member generally includes an elongated core wire having a tapered distal portion, a coil encasing at least part of the tapered distal portion of a core wire. The coil has an expanded section, and a reference member disposed therein which is secured to the coil proximally and distally of the expanded coil section. The core wire is secured to the coil at a location distally of the expanded section but proximally to the distal tip of the coil. Relative axial movement between the core wire and the coil causes expansion or contraction of the expanded coil section which results in tip deflection.

26 Claims, 3 Drawing Sheets

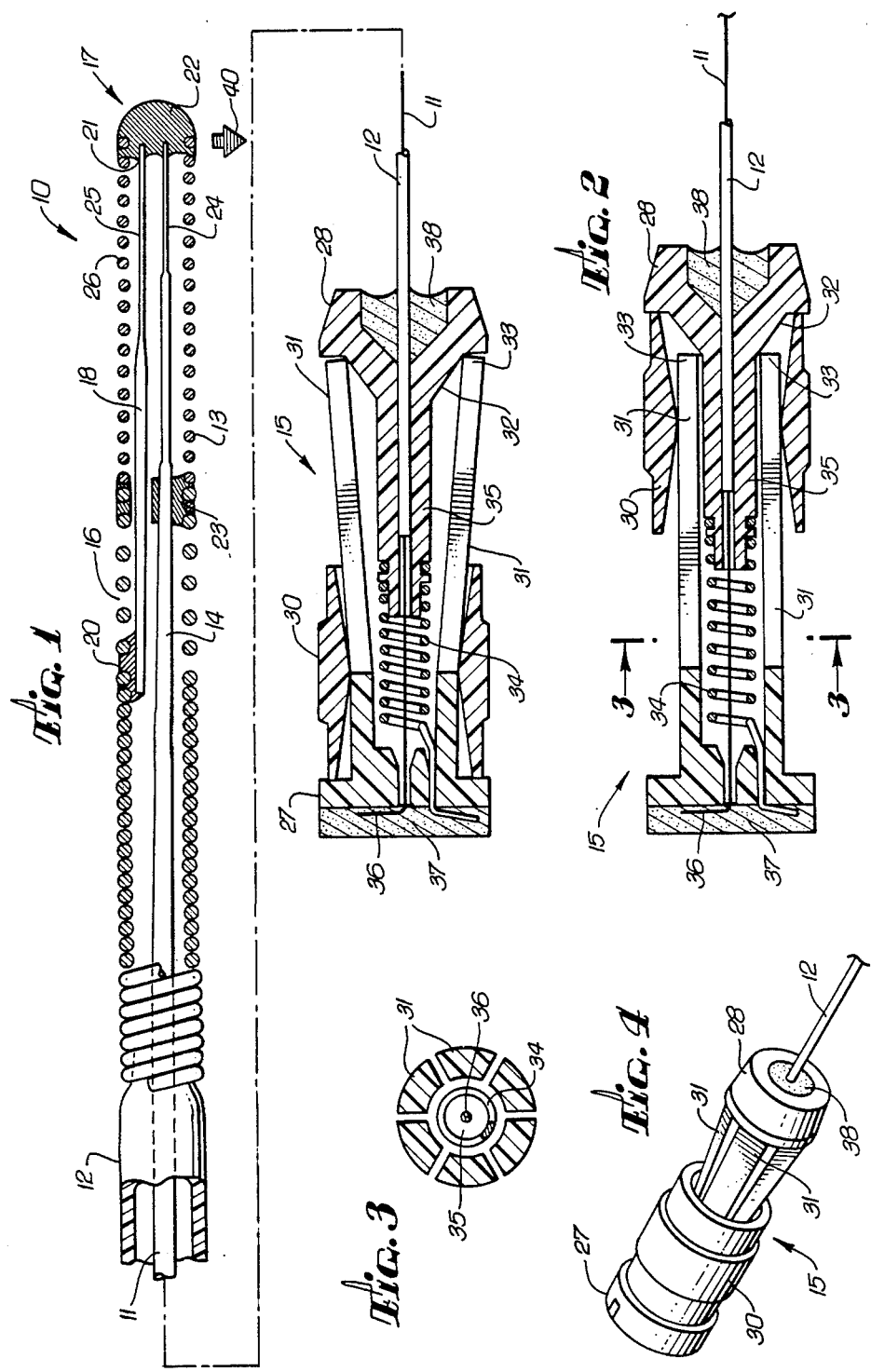

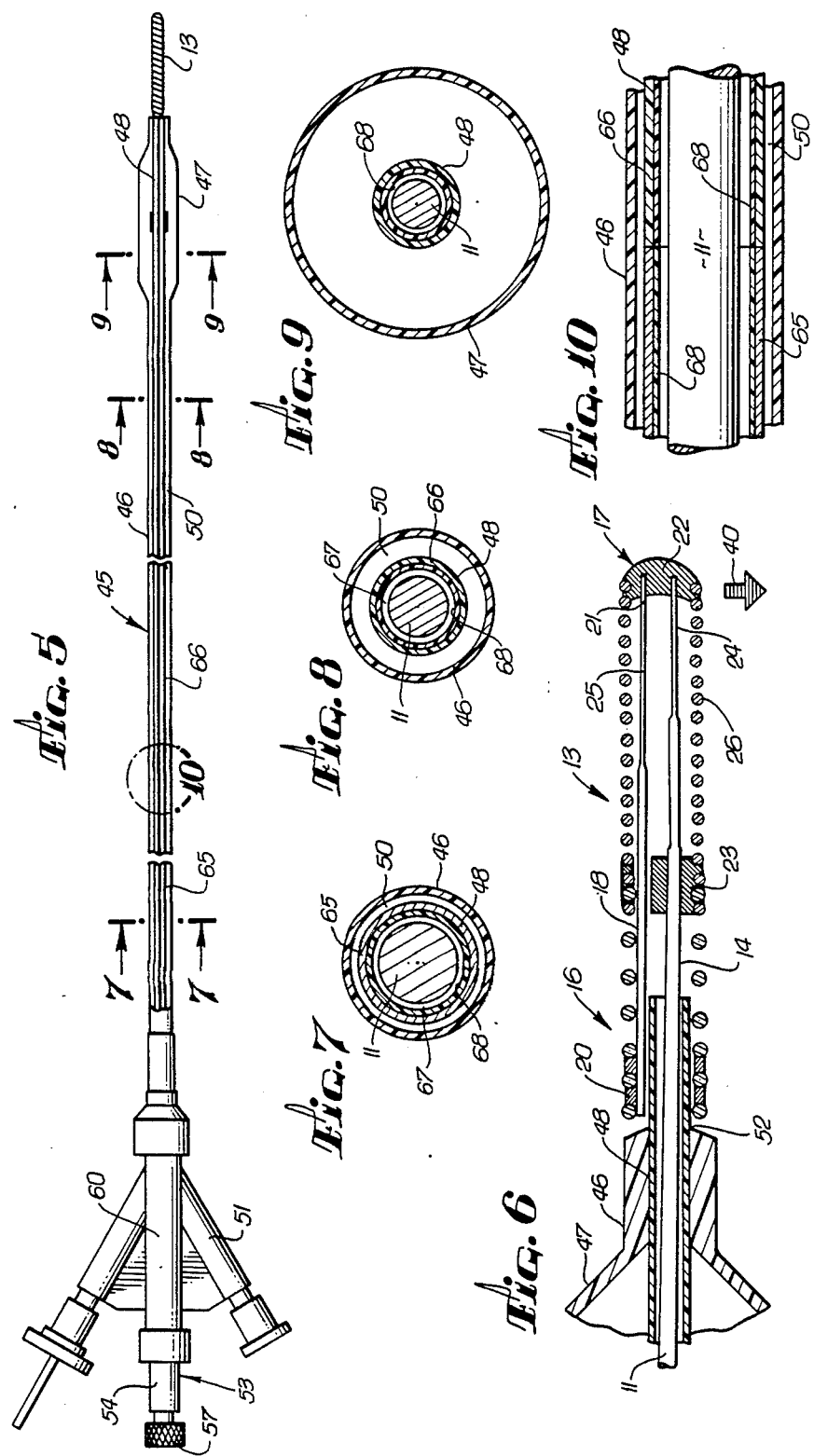

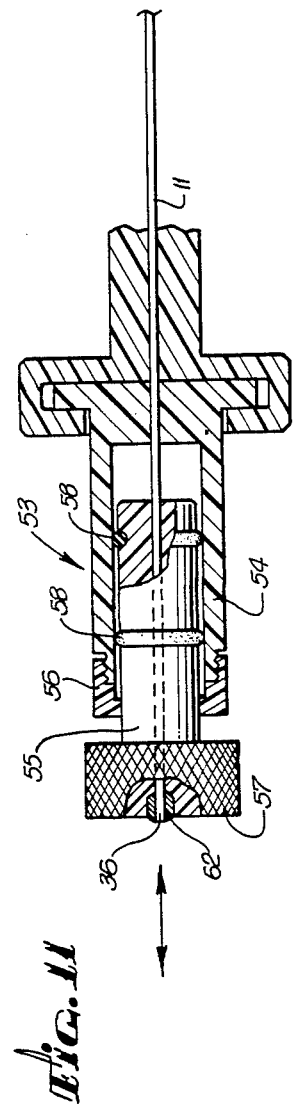
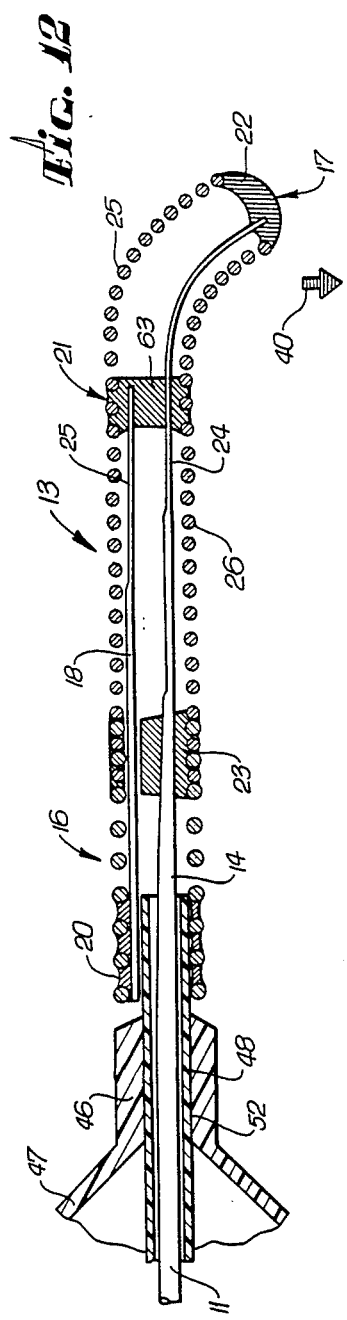

GUIDING MEMBER WITH DEFLECTABLE TIP

This invention generally relates to vascular catheters and particularly to guiding members for the placement of catheters within a patient's vascular system in procedures such as percutaneous transluminal coronary angioplasty (PTCA).

In typical PTCA procedures a guiding catheter having a preformed distal tip is percutaneously introduced into the cardiovascular system of a patient and advanced therein until the distal tip thereof is in the coronary artery. A guidewire is introduced through the guiding catheter and advanced into the patient's coronary vasculature until the distal end of the guidewire crosses the lesion to be dilated. A dilatation catheter having an inflatable balloon on the distal portion thereof is advanced over the previously introduced guidewire, with the guidewire slidably disposed within an inner lumen of the dilatation catheter, until the dilatation balloon is properly positioned across the lesion. Once in position across the lesion, the balloon is inflated to a predetermined size with radiopaque liquid at relatively high pressures to compress the atherosclerotic plaque of the lesion against the inside of the artery wall. The balloon is then deflated so that the dilatation catheter can be removed and blood flow resumed through the dilated artery.

Steerable dilatation catheters with built-in guiding members are being used with greater frequency because the deflated profiles of such catheters are generally much smaller than conventional dilatation catheters and a smaller profile allows the catheter to cross tighter lesions and to be advanced much deeper into the patient's coronary anatomy. Additionally, the use of steerable low-profile dilatation catheters shortens the time for the angioplasty procedures because there is no need to first insert a guidewire and then insert a conventional dilatation catheter over the previously inserted guidewire.

Further details of dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson), U.S. Pat. No. 4,538,622 (Samson et al.); U.S. Pat. No. 4,582,185 (Samson); U.S. Pat. No. 4,616,652 (Simpson); and U.S. Pat. No. 4,638,805 (Powell) which are hereby incorporated herein in their entirety by reference thereto.

Guidewires and steerable catheters generally have shapable tips so that once a shaped or bent tip is pushed beyond the guiding catheter the tip assumes the preformed shape which aids in the steering of the guidewire or the steerable catheter through the coronary vasculature of the patient. However, there has been little success in accurately controlling the shape of the distal tip of a guidewire or steerable catheter once the guidewire or steerable catheter is disposed within the patient's arterial system. What has been needed and heretofore unavailable is a means to easily and accurately control tip deflection of torqueable guidewires or steerable catheters from the proximal end thereof when the guidewire or steerable catheter is in the patient's arterial system. The present invention satisfies that need.

SUMMARY OF THE INVENTION

The present invention is directed to a torqueable guidewire or guiding member for vascular catheters having an easily deflectable tip which can be operated from the proximal end of the guidewire when the guidewire is being advanced through a patient's arterial system. The guide means is particularly suitable for dilatation catheters used in PTCA procedures.

The guidewire in accordance with the present invention generally has an elongated core element which preferably has a tapered distal portion to provide selective flexibility at the distal end. A helical coil is disposed about at least the most distal portion of the core element and is provided with an expanded coil section at a location proximally of the distal end thereof. The helical coil is secured to the core element at an intermediate location distal to the expanded coil section and proximal to the distal end of the coil The proximal end of the coil is preferably joined to the distal end of an outer tubular guide element, such as a hypotube, which extends about the core element to the proximal end of the guidewire or guiding member. An elongated reference element is also disposed within the coil and secured adjacent to an inner side thereof at locations proximally and distally of the expanded coil section. Means are provided at the proximal end of the guiding member to effect relative axial movement of the core element with respect to the outer tubular guide element, such as the hypotube or the coil, to change the spacing between the turns of the expanded coil section, i.e., compressing or expanding the expanded coil section and thereby causing the deflection of the tip of the guiding member.

The guiding member of the present invention can be employed as an independent guidewire or it can be incorporated or fixed within a steerable dilatation catheter. It provides for effective tip deflection yet it maintains the torqueing capabilities of the guiding member without interference between the individual components thereof. These and other advantages of the invention will become more apparent from the following detailed description thereof along with the accompanying exemplary drawings.

BRIEF DESCRIPTION OF THE DRAWINGS

FIG. 1 is a partial cross-sectional view of a guidewire embodying features of the invention;

FIG. 2 is a longitudinal cross-sectional view of the proximal end of the guidewire shown in FIG. 1 with the manipulator or handle in a position to cause the deflection of the distal tip of the guidewire;

FIG. 3 is a cross-sectional view taken along the lines 3—3 shown in FIG. 2;

FIG. 4 is a perspective view of the manipulator or handle shown in FIGS. 1 and 2;

FIG. 5 is a partial cross-sectional view of a low-profile steerable dilatation catheter having a fixed guide member embodying features of the invention;

FIG. 6 is a longitudinal cross-sectional view of the distal tip of the low-profile steerable dilatation catheter shown in FIG. 5;

FIGS. 7, 8, and 9 are enlarged transverse cross-sectional views taken along the lines 7—7, 8—8, and 9—9 shown in FIG. 5;

FIG. 10 is an enlarged view of the catheter shown in the circle in FIG. 5;

FIG. 11 is a longitudinal cross-sectional view of the manipulator or handle at the proximal end of the catheter shown in FIG. 5; and FIG. 12 is a is a longitudinal cross-sectional view of the distal tip of an alternate embodiment of a low-profile steerable dilatation catheter embodying features of the invention.

DETAILED DESCRIPTION OF THE INVENTION

FIG. 1 illustrates a guidewire 10 embodying features of the invention which generally comprises a core element 11, an outer tubular element 12 disposed about the core element and extending along a substantial part of the length thereof, a helical coil 13 disposed about the distal tapered portion 14 of the core element and a handle or manipulator element 15 secured to the proximal end of the core element for the manipulation thereof. The coil 13, disposed about the tapered distal portion 14 of the core element 11, is provided with an expanded section 16 at an intermediate location spaced proximally from the distal tip 17 of the guidewire 10. The expanded section 16 should be expanded at least 50%, preferably at least 70% of the stacked distance thereof.

The proximal end of coil 13 is joined to the distal end of the outer tubular element 12, preferably hypotubing, which extends proximally to the handle 15. A reference element 18 is disposed within the coil 13 and is joined to an inner side thereof at a first location 20 proximal to the expanded section 16 and at a second location 21 distally thereof, which in this case is the plug 22. The core element 11 is joined to the coil 13 at an intermediate location 23 between the distal end of the expanded portion 16 and the distal tip 17. Preferably, the core 11 is joined to the coil 13 immediately adjacent to the distal end of the expanded section 16. The core 11, the outer tubular element 12, the coil 13, and the reference element 18 may be joined by brazing, soldering or other suitable means.

As shown in FIG. 1, the tapered portion of core element 11 is preferably flattened in one or more stages 24 to provide improved flexibility and stiffness transition in the tip thereof. The reference element 18 is preferably a ribbon also flattened in one or more stages 25 in the distal direction to also improve flexibility. At least the portion 26 of the coil 13 distally of the expanded section 16 should be formed of suitable radiopaque material, such as platinum, tungsten, and alloys thereof, to facilitate the fluoroscopic observation thereof during angioplasty procedures. The distal portion 26 may be provided with an expanded set (e.g., 10% of the stacked length) as shown to provide greater tip flexibility. Plug 22 at the distal tip 17 of the guidewire 10 is made from gold, platinum, tungsten or other suitable radiopaque materials for essentially the same reason, i.e., improved fluoroscopic observation thereof.

The manipulator or handle 15 at the proximal end of guidewire 10 generally comprises a proximal portion 27 a distal portion 28 and a collar 30 which is slidably mounted about the legs 31 which extend distally of proximal portion 27. The distal portion 28 has a cammed surface 32 which slidably engages distal ends 33 of the legs 31. A helically coiled spring 34 is disposed in part about the proximal projection 35 on the distal portion 28. The proximal end 36 of the core element 11 passes through the handle 15 and is fixed by a suitable adhesive 37 to the proximal portion 27 of the handle 15. The distal end 28 of the handle 15 is joined by a suitable adhesive 38 to outer tubular element or hypotube 12 which passes therethrough. The proximal end of the spring wire 34 is secured to the proximal portion 27 by adhesive 37, as shown. The handle parts 27, 28, and 30 can be formed of suitable plastic material such as ABS.

The operation of the handle manipulator 15 is best shown in FIGS. 1 and 2. In FIG. 1, the slidable collar 30 is in its most proximal position with the coiled wire spring 34 being under slight tension to urge the proximal portion 27 against the distal portion 28. In FIG. 2, the collar 30 has been slid to its most distal position urging the legs 31 radially inwardly, sliding the ends 33 thereof over cam surface 32. This movement causes the proximal portion 27 to be moved proximally with respect to the distal portion 28, thereby creating a differential longitudinal or axial movement between the core element 11 and the outer tubular element or hypotube 12 which effects the deflection of the distal tip 17 of the guidewire 10. When the collar 30 is moved to its most proximal position, as shown in FIG. 1, the tension on spring 34 returns the proximal section 27 to its original position which in turn returns the distal tip 17 to its original position.

The relative axial movement between the core 11 and the outer tubular element 12 compresses the expanded coil section 16 causing the reference member 18 to be thrust toward the tip 17. However, because the distal end of reference member 18 is secured to the plug 22, the reference member 18 bends toward the side of the coil 13 secured to the core element 11 causing tip deflection in that direction, as shown by the arrow 40. The individual turns of the coil 13 proximal to the expanded coil section 16, which are stacked adjacent to one another, and the hypotube 12 provide columnar support to the coil so that relative axial movement between the core element 11 and the hypotube 12 caused by the actuation of handle 15 will be transmitted to the distal end, resulting in the compression of expanded section 16 of the coil and the desired deflection of tip 17. It is preferred to coat the outer surface of the core 11 with lubricious material, such as polytetrafluoroethylene (Teflon), to reduce friction. If desired, the hypotube may be replaced by a continuation of the coil 13, provided the coils thereof proximal to the expanded section 16 are stacked adjacent to one another to provide columnar support.

The cam surface 32, is shown in FIGS. 1 and 2 in the form of a smooth truncated conical section which provides for a continuous relative movement of the core element 11 upon the movement of collar 30. However, the cammed surface 32 can be provided with a series of steps in order to provide a stepped axial movement of the core 11 with respect to the outer tubular element 12 so that the amount of tip deflection can be determined from the proximal end of the guidewire when the guidewire is in position within a patient.

Typical dimensions of the core element 11 shown in FIGS. 1 and 2 include a length of about 150 to 200 cm, a diameter (including any lubricious coating) which ranges from about 0.008 to about 0.018 inch (0.203–0.457 mm) at the proximal end, and at the distal end 22 of generally rectangular shape of 0.001 by 0.006 inch (0.0254 by 0.1524 mm) in transverse cross section. The length of the coil 13 and the outer tube is approximately the same as the core element 11. The expanded coil section 16 may vary in length from about 0.1 to about 0.75 preferably about 0.2 to about 0.4 cm, with the expansion ranging from about 50 to 100%, preferably about 70 to 100% of the stacked length thereof. The distal coil portion 26 is preferably formed from radiopaque wire of about 0.0025 inch (0.0635 mm) in diameter, whereas the expanded coil section 16 and the portion proximally thereof are formed from stainless steel wire about 0.003 inch (0.0762 mm) in diameter. Preferably, the mating ends of the coil sections are intertwined or threaded together then bonded by soldering, brazing, or other suitable means to the core element 11 at the intermediate location 23. The reference member 18 is preferably rectangularly shaped, formed of stainless steel and has proximal dimensions of 0.002 by 0.004 inch (0.051 by 0.102 mm) and distal dimensions of 0.001 by 0.006 inch (0.025 by 0.152 mm).

FIGS. 5-11 illustrate other presently preferred embodiments involving the incorporation of a guide member with a deflectable tip in accordance with the invention into a dilatation catheter. The dilatation catheter assembly 45 includes an outer tubular member 46 having an inflatable balloon 47 near the distal end thereof and an inner tubular member 48 disposed within the outer tubular member defining an annular passageway 50 therebetween for directing inflation fluid to the inflatable balloon 47. The proximal ends of the tubular members 46 and 48 are fixed to an adapter 51 and the distal ends thereof are secured together at 52 to prevent leakage of inflation fluid from the interior of the balloon 47.

The details of the deflectable tip construction of the catheter assembly 45 is best shown in FIG. 6, which has essentially the same construction as that shown in FIG. 1, except that in the embodiment shown in FIG. 6 the proximal end of coil 13 overlaps the distal end of the inner tubular member 48 and abuts the distal portion of the outer tubular member 46 which provides columnar support for the relative core-coil movement necessary for tip deflection. The dimensions of elements of the tip 17 are essentially the same as those for the embodiments shown in FIG. 1. The operation of the tip deflection for this embodiment is the same as guidewire 10. Core element 11 is pulled axially in the proximal direction causing the expanded coil section 16 to be compressed. Reference member 18 is thrust distally toward plug 22, but because it is secured thereto will cause the tip to deflect as shown by arrow 40.

FIG. 11 illustrates in detail the core element manipulator 53 shown in FIG. 5 which is fundamentally equivalent to the handle 15 in the embodiment shown in FIG. 1. It comprises a tubular extension 54, an insert 55 slidably disposed within the tubular extension 54, and a knob 57 on the proximal end of the insert 55 to facilitate movement of the core element 11 secured thereto. A pair of O-rings 58 are provided about the periphery of the insert 55 to seal the tubular extension 54 but allow axial movement of the insert 55 mounted therein to effect tip deflection. Screw cap 56 secures tubular extension 54 to the proximal end of adapter arm 60. The proximal end of core element 11 passes through arm 60 of adapter 51 and the insert 55 and is fixed to the knob 57 by a suitable adhesive 62. Pulling on the knob 57, as shown by arrow 40, causes tip deflection in the same manner, as described for the embodiment shown in FIG. 1.

A further tip modification is depicted in FIG. 12 wherein the reference element 18 is secured at a first location 20 proximal to expanded coil section 16 and at a second location 21 intermediate between the expanded coil section 16 and the plug 22. The distal end of the core element 11 is secured to the coil 13 at an intermediate location 23 proximal to the second location 27 but distally of the expanded coil section. Reference element 18 passes through the solder or brazement at intermediate location 23 where the core element 11 is joined to the coil 13. The distal portion of reference element 18 is secured to coil 13 at second location 21 by brazement or solder 63 which also joins the core 13. The distal end of the core element 11 is secured in the plug 22. The flattened section 24 of core 11 is shown manually bent to a desired shape. The distal section of the coil 13 is slightly expanded to provide flexibility.

The details of a particularly desirable inner tubular member 48 are shown in FIGS. 7-10. In this embodiment, inner tubular member 48 includes a hypotube 65 at the proximal portion thereof and secured to the distal end of the hypotube is a high-strength plastic tubular element 66 formed of polyimide. Preferably, both hypotube 65 and polyimide tubular element 66 are sized to have an inner lumen 67 along the length thereof with a diameter of not more than about 0.003 inch (0.0762 mm) greater than the diameter of the core element 11 disposed therein. This allows the inner tubular member 48 to provide support to the core element as described in copending application Ser. No. 000,646, filed Jan. 6, 1987, and assigned to the present assignee. Additionally, essentially the entire inner lumen 67 of the inner tubular member 48 has a lining 68 formed of a lubricous material, such as polytetrafluoroethylene, which is sold under the trademark Teflon by DuPont. The transverse cross-sectional views shown in FIGS. 7, 8, and 9 illustrate the variations in the length of the catheter assembly 45. The close fit of the inner tubular member 48 about the core 11 which provides added support and the Teflon lining which reduces considerably the force required to move the core 11 within the inner lumen 67 allows substantial reductions to be made in the diameter of the core element 11. For example, core elements with maximum diameters of 0.01 inch (0.254 mm) or less can be effectively employed with little risk of kinking during the manipulation thereof and with excellent transmission of torque from the proximal to the distal ends thereof.

The hypotube 65 may be made of suitable metallic material, such as type 304 stainless steel or nitinol which is a nickel-titanium alloy. Other suitable materials may be used. The polyimide tubular element 66 of the inner tubular member 48 is preferably Micro-Bore TM polyimide tubing manufactured by PolyMicro Technologies of Phoenix, Ariz., which has a very thin wall (i.e., 0.00075±0.00024 inch).

While the description of the present invention has been described herein primarily in terms of presently preferred embodiments, modifications and improvements can be made without departing from the scope thereof.

What is claimed is:
1. A guide member for vascular catheters having a deflectable distal tip comprising:
   a. an elongated tubular member having a distal end;
   b. an elongated core element disposed within the tubular member and having a tapered distal portion which extends out the distal end of the tubular member;
   c. disposed about the tapered distal portion of the core element which extends out of the distal end of the tubular member, a helical coil element which has a proximal and distal ends, which has an ex- panded coil section at a location proximal to and spaced from the distal end of the coil element, which is secured to the core element at a location distal to the expanded coil section and proximal to the distal end of the coil and which has a rounded plug at the distal end thereof;

d. an elongated reference element which is secured to an adjacent side of the helical coil element at a first location proximal to the expanded coil section and at a second location distal to the location where the coil section element is secured to the core element;

e. means to provide columnar support to the proximal end for the coil; and f. means to axially move the core element with respect to the coil element along the longitudinal axis thereof, such longitudinal movement causing the expanded coil section to change the spacing between the turns thereof along the side of the coil opposite to the side adjacent to the reference element resulting in the deflection of the distal tip of the guide member.

2. The guide member of claim 1 wherein the distal end of the reference element is secured to a rounded plug provided in the distal end thereof.

3. The guide member of claim 1 wherein the distal end of the reference element is secured to the coil element at a location between the location where the core element is secured to the coil element and the distal tip thereof.

4. The guide member of claim 1 wherein the tubular member is diametrically rigid and the proximal end of the coil element thereof is secured to the distal end of the tubular member.

5. The guide member of claim 4 wherein the means to move the core element comprises a generally elongated handle having proximal and distal portions, the proximal portion having a plurality of legs which angle radially outwardly and a collar slidably mounted about the legs, the distal portion having a cammed surface over which the distal ends of the legs slide when the collar is moved distally, the proximal end of the core element being secured to the proximal portion of the handle and the proximal portion of the outer tubular element being secured to the distal portion of the handle which has the coil secured to the distal end thereof.

6. The guide member of claim 4 wherein the outer tubular element is a hypotube.

7. The guide member of claim 4 wherein the outer tubular member is a proximal extension of the coil element.

8. The guide member of claim 1 wherein the expanded coil section has a length of about 0.1 to about 0.75 cm.

9. The guide member of claim 1 wherein the expanded coil section is expanded at least 50 % of the stacked coil length thereof.

10. The guide member of claim 9 wherein the expanded coil section is expanded from 50% to about 100% of the stacked coil length thereof.

11. The guide member of claim 9 wherein the expanded coil section is expanded from about 70% to about 100% of the stacked coil length thereof.

12. The guide member of claim 1 wherein the expanded coil section has a length of about 0.2 to about 0.4 cm.

13. The guidewire of claim 1 wherein the helical coil distal to the location where the core member is secured thereto is expanded.

14. A steerable dilatation catheter having a deflectable distal tip, comprising:

(a) an outer tubular member having an inflatable balloon near the distal end thereof;

(b) an inner tubular member having an inner lumen therein disposed within the outer tubular member and defining an annular passageway between the inner and outer tubular members to direct inflation liquid to the interior of the inflatable balloon;

(c) an elongated core element having a tapered distal portion and being disposed within the inner lumen of the inner tubular member with a tapered distal portion of the core element extending out of the distal end of the inner tubular member;

(d) disposed about the tapered distal portion of the core element which extends out of the distal end of the tubular member, a helical coil element which has proximal and distal ends, which has an expanded coil section at a location proximal to and spaced from the distal end of the coil element, which is secured to the core element at a location distal to the expanded coil section and proximal to the distal end of the coil element and which has a rounded plug at the distal end thereof;

(e) an elongated reference element which is secured to an adjacent side of the coil element at a first location proximal to the expanded coil section and at a second location distal to the location where the core element is secured to the coil element;

(f) means to provide columnar support to the proximal end of the coil; and (g) means to axially move the core element with respect to the coil element along the longitudinal axis thereof, such longitudinal movement causing the expanded coil section to change the spacing between the turns thereof along the side of the expanded coil opposite to the side adjacent to the reference member resulting in the deflection of the distal tip of the catheter.

15. The steerable dilatation catheter of claim 14 wherein the inner tubular member has an inner diameter of not more than about 0.003 inch greater than the diameter of the core element over a substantial length thereof.

16. The steerable dilatation catheter of claim 15 wherein the distal end of the reference element is secured to the rounded plug provided in the distal end thereof.

17. The steerable dilation catheter of claim 15 wherein the distal end of the reference element is secured to the coil element at a location intermediate between the location where the core element is secured to the coil element and the distal end of the coil.

18. The steerable dilatation catheter of claim 14 wherein the expanded coil section has a length of about 0.1 to about 0.75 cm.

19. The steerable dilatation catheter of claim 18 wherein the expanded coil section is expanded at least 50% of the stacked length thereof.

20. The steerable dilatation catheter of claim 18 wherein the expanded coil section is expanded from 50 to about 100% of the stacked length thereof.

21. The steerable dilatation catheter of claim 18 wherein the expanded coil section has a length of about 0.2 to about 0.4 cm.

22. The steerable dilatation catheter of claim 14 wherein the inner lumen of the inner tubular member is lined with a lubricious material.

23. The steerable dilation catheter of claim 15 wherein the lubricious material is polytetrafluoroethylene.

24. The steerable dilatation catheter of claim 14 wherein a distal portion of the inner tubular member is formed from polyimide and a proximal portion of the inner tubular member is formed from a hypotube.

25. The steerable dilatation catheter of claim 14 wherein the means for longitudinally moving the core element with respect to the coil element comprises a manipulator secured to an arm of an adapter through which the core passes, the manipulator comprising a tubular extension secured to the proximal end of the adapter arm through which the core element passes, an insert slidably disposed in the tubular extension, and a knob on the proximal end of the insert with the proximal portion of the core element secured to the knob.

26. The steerable dilatation catheter of claim 14 wherein the helical coil distal to the location where the core member is secured thereto is expanded.

* * * * *